United States Patent
Joosten et al.

(10) Patent No.: US 9,551,717 B2
(45) Date of Patent: Jan. 24, 2017

(54) METHOD FOR DIAGNOSING Q-FEVER USING A CELLULAR IMMUNOLOGICAL TEST

(75) Inventors: Leonardus Antonius Bernardus Joosten, Beuningen (NL); Mihai Gheorghe Netea, Nijmegen (NL); Johannes Willem Maarten van der Meer, Nijmegen (NL); Bart Julian Kullberg, Nijmegan (NL); Marcel van Deuren, Oeffelt (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 0 days.

(21) Appl. No.: 13/817,416

(22) PCT Filed: Aug. 16, 2011

(86) PCT No.: PCT/NL2011/050564
§ 371 (c)(1),
(2), (4) Date: Apr. 9, 2013

(87) PCT Pub. No.: WO2012/023852
PCT Pub. Date: Feb. 23, 2012

(65) Prior Publication Data
US 2013/0210038 A1  Aug. 15, 2013

Related U.S. Application Data

(60) Provisional application No. 61/374,313, filed on Aug. 17, 2010.

(30) Foreign Application Priority Data
Aug. 17, 2010  (EP) ..................... 10173056

(51) Int. Cl.
G01N 33/554 (2006.01)
G01N 33/68 (2006.01)

(52) U.S. Cl.
CPC ...... *G01N 33/6866* (2013.01); *G01N 33/6893* (2013.01); *G01N 2333/195* (2013.01); *G01N 2333/57* (2013.01)

(58) Field of Classification Search
None
See application file for complete search history.

(56) References Cited

PUBLICATIONS

Corstjens, et al., "A User-Friendly, Highly Sensitive Assay to Detect the IFN-Gamma Secretion by T Cells," Clinical Biochemistry, vol., 41, No. 6, pp. 440-444 (Jan. 3, 2008).
Delsing, C.E., et al., "Q Fever in the Netherlands: A Concise Overview and Implications of the Largest Ogoing Outbreak," The Netherlands Journal of Medicine, vol. 66, No. 9, pp. 365-367 (Oct. 1, 2008).
International Search Report of PCT/NL2011/050564 dated Sep. 28, 2011.

(Continued)

*Primary Examiner* — Ja'Na Hines
*Assistant Examiner* — Khatol Shahnan Shah
(74) *Attorney, Agent, or Firm* — Morgan, Lewis & Bockius LLP

(57) ABSTRACT

The present invention relates to a method for diagnosing Q-fever in a subject, the method comprising the steps of: (a) obtaining a sample from said subject, (b) contacting said sample with a source of a *Coxiella burnetii* antigen and (c) determining the expression level of a pro-inflammatory cytokine such as IFN-γ in said sample at the end of step (b).

**7 Claims, 1 Drawing S

(56) References Cited

PUBLICATIONS

Izzo A.A., et al., "Variation in Interferon-Gamma Responses to Coxiella Burnetii Antigens with Lymphocytes from Vaccinated or Naturally Infected Subjects," Clinical and Experimental Immunology, vol. 94, No. 3, pp. 507-515 (Dec. 1993).

Izzo, A.A., et al., "Analysis of the Cells Involved in the Lymphoproliferative Response to Coxiella Burnetii Antigens," Clinical and Experimental Immunology, vol. 85, No. 1, pp. 98-108 (Jul. 1991).

Izzo, A.A., et al., "Markers of Cell-Mediated Immunity After Vaccination With an Inactivated, Whole-Cell Q Fever Vaccine," The Journal of Infectious Diseases, vol. 157, No. 4, pp. 781-789 (Apr. 1988).

Tyczka, J., et al., "Differences in Cytokine mRNA Profiles Between Naïve and In Vivo-Primed Ovine PBMC After Exposure to Heat-Inactivated Coxiella Burnetii," Annals of the New York Academy of Sciences, vol. 990, pp. 460-467 (Jun. 2003).

Written Opinion of the European Patent Office as the International Searching Authority of PCT/NL2011/050564 dated Sep. 28, 2011.

Dellacasagrande, J. et al., "Coxiella burnetii survives in monocytes from patients with Q fever endocarditis: involvement of tumor necrosis factor," Infection and Immunity, vol. 68, No. 1, pp. 160-164 (Jan. 2000).

Honstettre, A. et al., "Dysregulation of cytokines in acute Q fever: role of interleukin-10 and tumor necrosis factor in chronic evolution of Q fever," Journal of Infectious Diseases, vol. 187, pp. 956-962 (Mar. 6, 2003).

Meghari, S. et al., "Coxiella burnetii stimulates production of Rantes and MCP-1 by mononuclear cells: modulation by adhesion to endothelial cells and its implication in Q fever," Eur. Cytokine Netw., vol. 17, No. 4, pp. 253-259 (Dec. 2006).

Pentilla, I.A. et al., "Cytokine dysregulation in the post-Q-fever fatigue syndrome," Q J Med., vol. 91, pp. 549-560 (May 11, 1998).

Pira, G., et al., Validation of a Miniaturized Assay Based on IFNg Secretion for Assessment of Specific T Cell Immunity, Journal of Immunological Methods, vol. 355, pp. 68-75 (Mar. 1, 2010).

Schneeberger, P., et al., "Real-Time PCR with Serum Samples is Indispensable for Early Diagnosis of Acute Q Fever," Clinical and Vaccine Immunology, vol. 17, No. 2, pp. 286-290 (Feb. 2010).

Summons to Attend Oral Proceedings for European Patent Application No. 11745844.8 dated Mar. 2, 2015.

Applicant's Response to Notice of Oral Proceedings for European Patent Application No. 11745844.8 dated Sep. 8, 2015.

Brief Communication from the European Patent Office for European Patent Application No. 11745844.8 dated Sep. 24, 2015 maintaining date of oral proceedings.

Applicant's Response Written Submission in Preparation of Oral Proceedings for European Patent Application No. 11745844.8 dated Oct. 16, 2015.

Brief Communication from the European Patent Office for European Patent Application No. 11745844.8 dated Nov. 6, 2015 cancelling the oral proceedings.

Results of Consulation from the European Patent Office for European Patent Application No. 11745844.8 dated Nov. 27 and 30, 2015.

Communication under Rule 71(3) EPC—Intention to Grant from the European Patent Office for European Patent Application No. 11745844.8 dated Dec. 8, 2015.

SEQUENCE LISTING

<160> NUMBER OF SEQ ID NOS: 4

<210> SEQ ID NO 1
<211> LENGTH: 501
<212> TYPE: DNA
<213> ORGANISM: homo sapiens

<400> SEQUENCE: 1

```
atgaaatata caagttatat cttggctttt cagctctgca tcgttttggg ttctcttggc      60
tgttactgcc aggacccata tgtaaaagaa gcagaaaacc ttaagaaata ttttaatgca     120
ggtcattcag atgtagcgga taatggaact cttttcttag gcattttgaa gaattggaaa     180
gaggagagtg acagaaaaat aatgcagagc caaattgtct cctttactt caaacttttt     240
```

-continued

```
aaaaacttta aagatgacca gagcatccaa aagagtgtgg agaccatcaa ggaagacatg      300
aatgtcaagt ttttcaatag caacaaaaag aaacgagatg acttcgaaaa gctgactaat      360
tattcggtaa ctgacttgaa tgtccaacgc aaagcaatac atgaactcat ccaagtgatg      420
gctgaactgt cgccagcagc taaaacaggg aagcgaaaaa ggagtcagat gctgtttcga      480
ggtcgaagag catcccagta a                                                501
```

<210> SEQ ID NO 2
<211> LENGTH: 166
<212> TYPE: PRT
<213> ORGANISM: homo sapiens

<400> SEQUENCE: 2

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 3
<211> LENGTH: 21
<212> TYPE: DNA
<213> ORGANISM: artificial
<220> FEATURE:
<223> OTHER INFORMATION: primer

<400> SEQUENCE: 3
ctcttggctg ttactgccag g                                                21

<210> SEQ ID NO 4
<211> LENGTH: 21
<212> TYPE: DNA
<213> ORGANISM: artificial
<220> FEATURE:
<223> OTHER INFORMATION: primer

<400> SEQUENCE: 4
ctccacactc ttttggatgc t                                                21

METHOD FOR DIAGNOSING Q-FEVER USING A CELLULAR IMMUNOLOGICAL TEST

CROSS REFERENCE TO RELATED APPLICATIONS

The present application is the 35 U.S.C. 371 National Stage of International Application Number PCT/NL2011/050564, filed Aug. 16, 2011, which claims the benefit of U.S. Provisional Application No. 61/374,313, filed Aug. 17, 2010 and claims priority from European patent application EP10173056.2, filed Aug. 17, 2010, the contents of each of which are incorporated herein by reference.

SEQUENCE LISTING SUBMISSION VIA EFS-WEB

A computer readable text file, entitled "031902-5005-US-SEQ_ST25.txt", created on or about 15 Feb. 2013, with a file size of about 4 KB contains the sequence listing for this application and is hereby incorporated by reference in its entirety.

FIELD OF THE INVENTION

The present invention relates to a method for diagnosing Q-fever in a subject, using the determination of a pro-inflammatory cytokine expression level such as interferon-gamma.

BACKGROUND OF THE INVENTION

Q-fever is a systemic infection caused by the intracellular bacterium *Coxiella burnetii*. The infection is common in animals, especially livestock, and transmitted to humans mainly through the airborne route. The disease presentation varies widely, ranging from asymptomatic infection, acute febrile illness most often with pneumonia, chronic complicated Q-fever (mainly with endocarditis or vascular infection) and post-Q-fever fatigue.

Currently The Netherlands is faced with the most extensive outbreak of Q-fever, related to goat farms. Since 2007, an increasing number of human cases have occurred. The diagnosis is based on a history of exposure, clinical examination and on PCR and serology. Due to the difficulty in culturing *Coxiella burnetii* in the laboratory, the variation in the antibody response, and the difficulties to standardize serology, the laboratory diagnosis is often not easy. Quite some weight is being given to the phase dependent antibodies, where phase 1 antibodies are seen in chronic infection and the phase 2 antibodies are related to acute infection. With accumulating experience in complicated cases in the current Dutch epidemic, we have experienced that the results of the serology may be equivocal.

If diagnosed in the acute stage, the disease can be cured with a relatively short course of the antibiotic doxycyclin, but chronic Q-fever is a much more difficult-to-treat infection. Chronic Q-fever has a high mortality rate. A special situation is Q-fever in pregnancy, in which the risk for the unborn and the management is not entirely clear.

A special area where the diagnostic tool is critical is the Q-fever vaccination of humans. Currently, patients are screened with serology and a skin test, and only if both tests are negative, vaccination is regarded a safe procedure. The skin test is not easy to perform and laborious. Its sensitivity and specificity are unknown.

There is a need for a specific and sensitive method for diagnosing Q-fever in a subject, circumventing all the drawbacks of existing methods. In addition, the current tests (with the possible exception of the skin test) do not assess the state of specific cellular immunity, which is needed for cure of the infection.

DESCRIPTION OF THE INVENTION

Diagnosis Method

Figure 1:
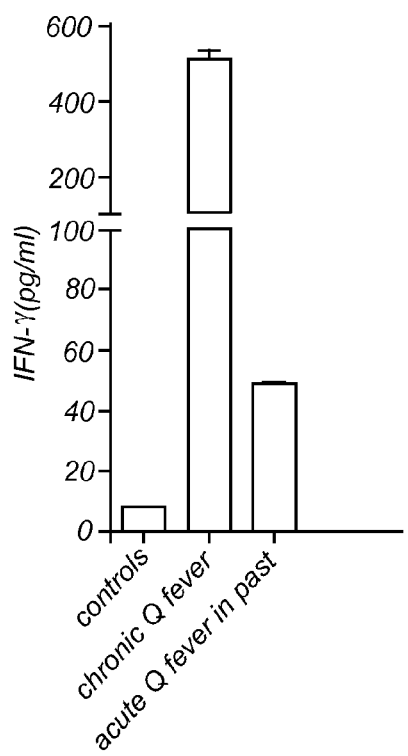
FIG. 1: Whole blood from patients and controls was diluted 1:5 in RPMI and exposed to *Coxiella burnetii* antigens for 48 hours. In the supernatant immunoreactive Interferon gamma (IFNγ) was measured. Controls exhibited baseline production while chronic Q fever patients showed a high response and patients recovered from uncomplicated acute Q fever showed an intermediate response.

In a first aspect, the invention relates to a method for diagnosing Q-fever in a subject, the method comprising the steps of:
(a) obtaining a sample from said subject,
(b) contacting said sample with a source of *Coxiella burnetii* antigens and,
(c) determining the expression level of a pro-inflammatory cytokine in said sample at the end of step (b).

A pro-inflammatory cytokine is a cytokine that is able to promote systemic inflammation. A pro-inflammatory cytokine is preferably selected from the group consisting of IL-1β, or IFNγ, IL-6, and IL-17. IFNγ is a preferred pro-inflammatory cytokine in this context.

In the context of the invention, "diagnosing Q-fever" preferably means that a diagnosis is reached in:
Subjects with acute Q-fever infection
Subjects with chronic Q-fever
Subjects with post-Q-fever fatigue
Subjects who have had Q-fever infection and therefore should not receive Q-fever vaccine. Subjects that have not been infected with *Coxiella burnetii* will not produce these cytokines in vitro. As soon as a detectable level of a pro-inflammatory cytokine has been detected in step c), acute Q-fever infection or chronic Q-fever or post-Q-fever fatigue has been diagnosed in a subject.

In this context, acute Q-fever infection means recently acquired infection caused by *Coxiella burnetii*. "Recently" may mean at least 1, 2, 3, 4, 5, 6, 7 days or longer but shorter than 30 days.

In this context, chronic Q-fever means that the illness caused by *Coxiella burnetii* exists since 30 days or more.

In this context, post-Q-fever fatigue means severe fatigue after infection caused by *Coxiella burnetii*.

A symptom/parameter associated with acute Q-fever infection is fever, pneumonia or hepatitis.

A subject with acute Q-fever infection may be diagnosed using the assay of the invention. Without wishing to be bound to any theory, we expect an intermediate cytokine response may be detected in such a subject. The assay is rapid and has added value over the current serology.

A subject with chronic Q-fever may be diagnosed using the assay of the invention. Without wishing to be bound to any theory, we expect a higher cytokine response may be detected in this subject than a subject with acute Q-fever infection. The assay is rapid and has added value over the current serology.

In the context of the invention, a subject may be a human being or an animal. The animal may be goat. The diagnosis method may be applied as often as necessary in a subject. If the subject is a human being, the subject may be a person suspected to have a high risk of having or developing chronic Q-fever, for example due to the fact that this subject lives in a region wherein Q-fever is common such as the Netherlands, France or Australia. In an embodiment, it is not known whether a subject has been infected with a Q-fever bacterium *Coxiella burnetii*. If the subject is an animal, e.g., a goat, the invention is used to make the diagnosis of infection caused by *Coxiella burnetii* in the animal. In an embodiment, a subject to be diagnosed using a method of the invention has not been vaccinated with a vaccine against Q-fever.

In a preferred method, Q-fever is diagnosed when step (c) leads to the finding of a detectable or increased expression level of a pro-inflammatory cytokine Optionally in a method of the invention, one may compare the expression level of a pro-inflammatory cytokine as determined in step (c) with a reference value for said expression level, the reference value preferably being the average value for said expression level in a control sample. In the context of the invention, "a reference value" for the expression level of said cytokine is preferably the average value for said expression level in a control sample. A control sample may be derived from a control subject or from control subjects or from the culture medium used for step (b). A control subject may be a subject who does not live in a region at risk or who does not have animal contact. "A reference value" may mean that no cytokine level is detectable. The assessment of the expression level of a pro-inflammatory cytokine may be directly realised at the protein expression level (quantifying the amount of said cytokine protein), and/or indirectly by quantifying the amount of a nucleotide sequence encoding for said pro-inflammatory cytokine. A preferred nucleotide acid sequence encoding IFN-γ is as SEQ ID NO:1. A preferred corresponding IFN-γ amino acid sequence is given as SEQ ID NO:2. The skilled person will understand that it is possible to isolate multiple isoforms of IFN-γ depending on the subject or species to be tested.

In a preferred embodiment, IFN-γ to be quantified has:
at least 60%, 70%, 80%, 90%, 95%, or 100% identity with SEQ ID NO:2 and/or
is encoded by a nucleotide acid sequence which has at least 60%, 70%, 80%, 90%, 95%, or 100% identity with SEQ ID NO:1.

In another preferred embodiment, a nucleotide acid sequence encoding IFN-γ, as a pro-inflammatory cytokine as described herein) to be quantified has:
at least 60%, 70%, 80%, 90%, 95%, or 100% (identity with SEQ ID NO:1 and/or
encodes an amino acid sequence of IFN-γ that has at least 60%, 70%, 80%, 90%, 95%, or 100% identity with an amino acid sequence encoded by SEQ ID NO:1.

Identity is later herein defined. The quantification of the amount of a nucleotide sequence encoding IFN-γ and/or another pro-inflammatory cytokine as described herein is preferably performed using classical molecular biology techniques such as (real time) PCR, arrays or northern analysis. In this embodiment, a nucleotide sequence encoding IFN-γ (and/or another pro-inflammatory cytokine as described herein means a messenger RNA (mRNA). Alternatively, according to another preferred embodiment, in the diagnosis method the expression level of IFN-γ and/or another pro-inflammatory cytokine as described herein is determined directly by quantifying the amount of IFN-γ and/or another pro-inflammatory cytokine Quantifying a polypeptide amount may be carried out by any known technique. Preferably, a polypeptide amount is quantified using a molecule that specifically binds to IFN-γ (and/or to another pro-inflammatory cytokine as described herein). Preferred binding molecules are selected from: an antibody, which has been specifically raised for recognizing IFN-γ (and/or to another pro-inflammatory cytokine as described herein), any other molecule which is known to specifically bind IFN-γ (and/or to another pro-inflammatory cytokine as described herein). Such antibody could be used in any immunoassay known to the skilled person such as western blotting, or ELISA (Enzyme-Linked Immuno Sorbent Assay) or FACS (Fluorescence Activated Cell Sorting) using latex beads. The preparation of an antibody is known to those skilled in the art. A short explanation of methods that could be used to prepare antibodies is later herein given. In the context of the invention, any other molecule known to bind IFN-γ (and/or to another pro-inflammatory cytokine as described herein) may be a nucleic acid, e.g. a DNA regulatory region, a polypeptide, a metabolite, a substrate, a regulatory element, a structural component, a chaperone (transport) molecule, a peptide mimetic, a non-peptide mimetic, or any other type of ligand. Mimetic is later herein defined. Examples of molecules known to bind a pro-inflammatory cytokine such as IFN-γ, include a receptor of said pro-inflammatory cytokine such as the IFN-γ receptor, an antibody directed against said pro-inflammatory cytokine such as IFN-γ. Binding of a pro-inflammatory cytokine such as IFN-γ to a second binding molecule may be detected by any standard methods known to those skilled in the art. Suitable methods include affinity chromatography co-electrophoresis (ACE) assays and ELISA. The skilled person will understand that alternatively or in combination with the quantification of a nucleic acid sequence encoding a pro-inflammatory cytokine such as IFN-γ and/or a corresponding polypeptide, the quantification of a substrate of a corresponding polypeptide or of any compound known to be associated with a function or activity of a corresponding polypeptide or the quantification of a function or activity of a corresponding polypeptide using a specific assay is encompassed within the scope of the diagnosis method of the invention. For example, trans-activation of a target gene by a pro-inflammatory cytokine such as IFN-γ or a molecule which is able to bind a pro-inflammatory cytokine such as IFN-γ—(i.e. a IFN-γ-binding molecule) can be determined and quantified, e.g., in a transient transfection assay in which the promoter of the target gene is linked to a reporter gene, e.g., P-galactosidase or luciferase. Such evaluations can be done in vitro or in vivo or ex vivo.

In a method of the invention, a sample from a subject is used. A method of the invention is therefore an in-vitro or ex-vivo method. A sample preferably comprises or consists of a fluid obtained from a subject. More preferably, a fluid comprises or consists of or is selected from: urine, blood, spinal cord fluid, saliva, semen, or bronchoalveolar lavage. A preferred fluid is, comprises, consists of or is derived from blood. Blood may be diluted before being further used. The dilution may be 1:4, 1:5 or 1:6 in culture medium or a buffered solution.

In a method of the invention, said obtained sample of step (a) is subsequently contacted with a source of a *Coxiella burnetii* antigen. The choice of the antigen is dependent on prevalent *Coxiella burnetii* strains in different areas of the world The contact may have a duration of 1, 2, 3, 4, 5, 6, 7, 8, 12, 24, 30, 48, 60, 70, 80, 90, 93, 96, 100, 110 hours, or more. Preferably the contact has a duration of 4-96 hours. This contact step may be a culture step in a culture medium such as RPMI 1640.

Figure 2:
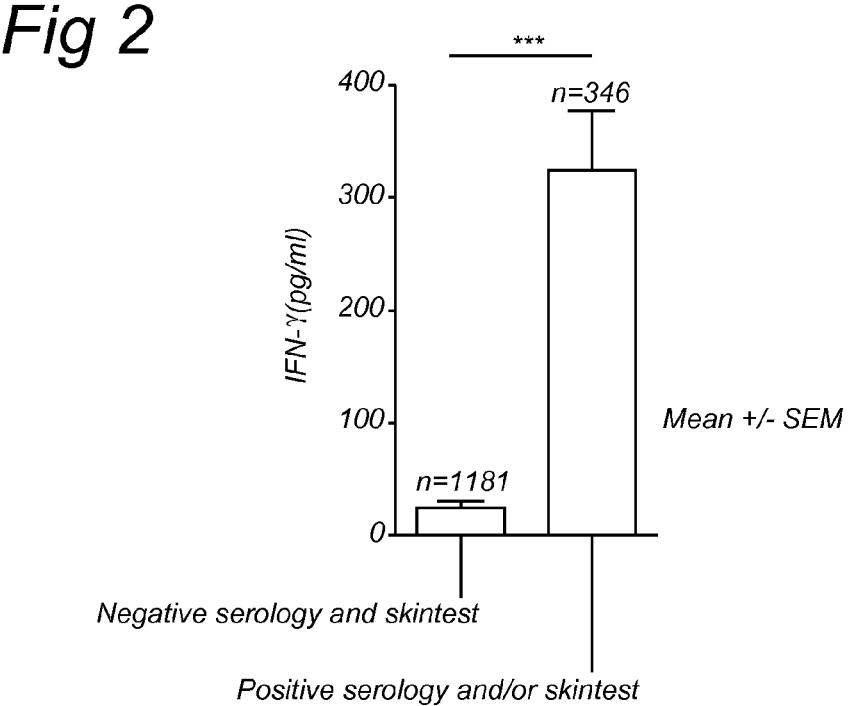
FIG. 2: Whole blood from individuals (n=1527) was diluted 1:5 in RPMI and exposed to heat killed *Coxiella burnetii* for 24 hours. In the supernatant immunoreactive Interferon gamma (IFNγ) was measured. Controls (1181) exhibited baseline production while individuals (n=346) exposed previously to *Coxiella burnetii* showed a high response.

A source of a *Coxiella burnetii* antigen may mean that a whole *Coxiella burnetii* cell is being used. In a preferred embodiment, a whole *Coxiella burnetii* cell is heat-inactivated or formalin fixated. Heat-inactivated could be replaced by heat-killed. The skilled person knows how to obtain heat-inactivated or formalin fixated *Coxiella burnetii* cells. Heat-inactivated cells are preferably prepared by heating at 95, 96, 97, 98 or 99° C. for 20, 25 or 30 minutes. More preferably heat-inactivated cells are prepared by heating at 99° C. for 30 minutes. Formalin fixated cells may be obtained by contacting the cells with formaldehyde for 40, 50, 60 minutes. More preferably, cells are contacted or transferred to 4% formaldehyde for one hour. Subsequently cells are washed several times with PBS (Phosphate Buffered Saline) buffer. Alternatively, part of a *Coxiella burnetii* cell may be used. A part of a *Coxiella burnetii* cell is preferably an antigenic part thereof; comprises or consists of an antigen. An antigen may be a protein, a digest of the protein and/or a fragment thereof, which may be in a purified form or may be comprised within a crude composition, preferably of biological origin, such as a lysate, sonicate or fixate of a *Coxiella burnetii*. Alternatively, an antigen may be chemically synthesized or enzymatically produced in vitro. The source of a protein, or fragment thereof as antigen, may also be a nucleic acid encoding said, or fragment thereof, from an RNA or DNA template. In a preferred embodiment, a source of a *Coxiella burnetii* antigen is a whole *Coxiella burnetii* cell or an antigen from said cell. The use of a whole *Coxiella burnetii* cell is attractive and preferred above the use of a part of a *Coxiella burnetii* cell for at least two reasons. The use of a whole *Coxiella burnetii* cell is easier and cheaper for the skilled person. There is no need to identify and subsequently synthetize suitable parts (i.e. antigenic parts) of a *Coxiella burnetii* cell. In addition, by using a whole *Coxiella burnetii* cell, all potential suitable part (i.e. all antigens) of a *Coxiella burnetii* cell are present. The diagnostic method is therefore expected to be far more sensitive and efficient than a corresponding diagnostic method carried out using a given antigen. Very promising results were obtained using heat-inactivated whole *Coxiella burnetii* cell (FIG. 2).

Subsequently, the expression level of a pro-inflammatory cytokine such as IFN-γ is determined in said sample at the end of the contact step of step (b). In a preferred embodiment, at the end of the contact step, the supernatant is isolated by centrifugation and the nucleotide sequence or the protein of a pro-inflammatory cytokine such as IFN-γ is determined by a skilled person using known methods. The centrifugation may be at 1200 rpm at 4° C. Alternatively, one may add a detergent to the sample at the end of step b). Several detergents could be used such as Triton X 0.1%. Adding a detergent is attractive since it is expected that no centrifugation step is needed. One may determine the expression level of a pro-inflammatory cytokine in the sample comprising said detergent, which is also called a cell lysate.

In a more preferred diagnosis method, Q-fever is diagnosed when the expression of a pro-inflammatory cytokine such as IFN-γ is detectable or detected and optionally when the comparison leads to the finding of a detectable expression of a pro-inflammatory cytokine such as IFN-γ and/or an increase of its expression level. In control subjects and in control samples as defined before, IFN-γ (and any other pro-inflammatory cytokine) is generally not detectable.

Detection of the expression of a pro-inflammatory cytokine such as IFN-γ or an increase of its expression level and/or an increase or a detection of the expression level of a nucleotide sequence encoding a pro-inflammatory cytokine such as IFN-γ (or steady state level of a pro-inflammatory cytokine such as IFN-γ) is preferably defined as being a detectable expression level or a detectable change of the expression level of a pro-inflammatory cytokine such as IFN-γ and/or of a nucleotide sequence encoding a pro-inflammatory cytokine such as IFN-γ (or steady state level of the encoded a pro-inflammatory cytokine such as IFN-γ or any detectable activity thereof or detectable change in a biological activity thereof) using a method as defined earlier on as compared to the expression level of a pro-inflammatory cytokine such as IFN-γ and/or of a corresponding nucleotide sequence (or steady state level of the corresponding encoded pro-inflammatory cytokine such as IFN-γ) in a control subject or in a control. According to a preferred embodiment, detection or an increase of an activity of a pro-inflammatory cytokine such as IFN-γ is quantified using a specific mRNA assay for the gene encoding said pro-inflammatory cytokine such as IFN-γ as earlier defined herein. Preferably, an increase of the expression level of a nucleotide sequence encoding a pro-inflammatory cytokine such as IFN-γ means an increase of at least 5% of the expression level of said nucleotide sequence using PCR. Preferred primers used for the PCR are identified as Forward Primer 5'-CTCTTGGCTGTTACTGCCAGG-3' (SEQ ID NO:3); and Reverse Primer 5'-CTCCACACTCTTTTG-GATGCT-3' (SEQ ID NO:4). More preferably, an increase of the expression level of a nucleotide sequence means an increase of at least 10%, even more preferably at least 20%, at least 30%, at least 40%, at least 50%, at least 70%, at least 90%, at least 150%, or more.

Preferably, an increase of the expression level of a pro-inflammatory cytokine such as IFN-γ means an increase of at least 5% of the expression level of a pro-inflammatory cytokine such as IFN-γ using western blotting and/or using ELISA or a suitable assay. More preferably, an increase of the expression level of a polypeptide means an increase of at least 10%, even more preferably at least 20%, at least 30%, at least 40%, at least 50%, at least 70%, at least 90%, at least 150%, or more.

Preferably, an increase of an activity of a pro-inflammatory cytokine such as IFN-γ means an increase of at least 5% of the polypeptide activity using a suitable assay. More preferably, an increase of the polypeptide activity means an increase of at least 10%, even more preferably at least 20%, at least 30%, at least 40%, at least 50%, at least 70%, at least 90%, at least 150% or more.

In a most preferred diagnostic method, Q-fever is diagnosed when the detection or comparison leads to the finding of a detectable level or an increase of the level of expression of a pro-inflammatory cytokine such as IFN-γ or an increase or a detection of the expression level of a nucleotide sequence encoding a pro-inflammatory cytokine such as IFN-γ, said detection or increase being detected at the level of the amino acid sequence of a pro-inflammatory cytokine such as IFN-γ, more preferably an increase of at least 5% of the expression level of said pro-inflammatory cytokine such as IFN-γ using ELISA as defined herein.

The method of the invention is attractive since the diagnosis is reached with more certainty. Furthermore, this method is non-invasive, simple, reproducible, sensitive, specific, and time and cost efficient.

Assay Device

In a second aspect, an assay device is provided for diagnosing Q-fever in a subject, wherein said device comprises a molecule which specifically binds a pro-inflammatory cytokine such as IFN-γ. This device may be used in a diagnosis method of the invention. Any subject or physician could use this device at office/home, repeat the use of such device as often as necessary.

The type of molecules that are known to specifically bind a pro-inflammatory cytokine such as IFN-γ have already been earlier described herein. In a preferred embodiment, a molecule which specifically binds a pro-inflammatory cytokine such as IFN-γ and which is present in the device is an antibody.

In a preferred embodiment, an assay device is a lateral flow test strip also known as dipstick, preferably, though not necessarily, encased in a housing, designed to be read by the subject, and the assay is a sandwich immunoassay. Such devices are impregnated with reagents that specifically indicate the presence of a given molecule, here a pro-inflammatory cytokine such as IFN-γ by changing colour upon contact with a sample. Preferred subject's samples have already been defined herein. An antibody is preferably labelled by conjugation to a physically detectable label, and upon contacting with a sample containing a pro-inflammatory cytokine such as IFN-γ forms a complex. Said antibody-pro-inflammatory cytokine complex, such antibody-IFN-γ complex is then contacted with a second antibody, which recognizes said first antibody and which is immobilized on a solid support within the device. A second antibody captures said antibody-pro-inflammatory cytokine complex or antibody-IFN-γ complex to form an antibody-pro-inflammatory cytokine-antibody sandwich complex or an antibody-IFN-γ-antibody sandwich complex, and the resulting complex, which is immobilized on the solid support, is detectable by virtue of the label. A test strip may then be inserted into a reader, where a signal from said label in the complex is measured. Alternatively, a test strip could be inserted into the reader prior to addition of the sample. Alternatively and according to a preferred embodiment, the presence of a pro-inflammatory cytokine such as IFN-γ is visualised by a subject as a change of colour of at least a part of a device. Dipsticks are usually made of paper or cardboard. Usually additional molecules are present in a device as a positive or negative control. A typical positive control could be an antibody recognizing a molecule which is known to be present in a sample to be tested. A typical negative control could be an antibody recognizing a molecule which is known to be absent in a sample to be tested.

Sequence Identity

"Sequence identity" is herein defined as a relationship between two or more amino acid (polypeptide or protein) sequences or two or more nucleic acid (polynucleotide) sequences, as determined by comparing the sequences. The identity between two amino acid or two nucleic acid sequences is preferably defined by assessing their identity within a whole SEQ ID NO as identified herein or part thereof. Part thereof may mean at least 50% of the length of the SEQ ID NO, or at least 60%, or at least 70%, or at least 80%, or at least 90%.

In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg, Gln or Glu; Met to Leu or Ile; Phe to Met, Leu or Tyr; Ser to Thr; Thr to Ser; Trp to Tyr; Tyr to Trp or Phe; and Val to Ile or Leu.

Antibodies

Some aspects of the invention concern the use of an antibody or antibody-fragment that specifically binds to a pro-inflammatory cytokine such as IFN-γ. Methods for generating antibodies or antibody-fragments that specifically bind to a polypeptide are described in e.g. Harlow and Lane (1988, Antibodies: A Laboratory Manual, Cold Spring Harbor Laboratory Press, Cold Spring Harbor, N.Y.) and WO 91/19818; WO 91/18989; WO 92/01047; WO 92/06204; WO 92/18619; and U.S. Pat. No. 6,420,113 and references cited therein. The term "specific binding," as used herein, includes both low and high affinity specific binding. Specific binding can be exhibited, e.g., by a low affinity antibody or antibody-fragment having a Kd of at least about $10^{-4}$ M. Specific binding also can be exhibited by a high affinity antibody or antibody-fragment, for example, an antibody or antibody-fragment having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

General

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a method or an assay device as defined herein may comprise additional step(s), respectively component(s) than the ones specifically identified, said additional step(s), respectively component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one". All patent and literature references cited in the present specification are hereby incorporated by reference in their entirety. The following examples are offered for illustrative purposes only, and are not intended to limit the scope of the present invention in any way.

EXAMPLE

Method

Blood samples were taken from patients and healthy individuals in EDTA vacutainer tubes (Becton and Dickinson, Leiden, The Netherlands). From these samples 200 μl were diluted 1:5 in culture medium (RPMI 1640) and incubated in 24 wells tissue culture plates (Costar, Badhoevedorp, The Netherlands). As a stimulus, 100 ng/ml of formaldehyde-inactivated (i.e. formalin fixated) *Coxiella burnetii* phase 1 Henzerling Strain (CSL limited, Australia) was added to these cultures (FIG. 1). Formaldehyde-inactivated cells were prepared by transferring or incubating them with 4% formaldehyde for one hour. Subsequently cells were washed several times with PBS. No stimulus was added to the control cultures. The cultures were incubated at 37° C. and 5% CO2 for 48 hours. Heat-killed or heat-inactivated *Coxiella burnetii* 9 mile strain (CVI, Lelystad, The Netherlands) was used in the second study (FIG. 2). Identical protocol, except 24 hours incubation. Heat-inactivated cells were prepared by heating them at 99° C. for 30 minutes.

After this incubation period, the supernatants were harvested and centrifuged at 15000 g for 5 minutes, and thereafter stored at −20° C. until measurement of interferon γ (IFNγ). IFN γ was measured using a specific ELISA (Pelikine Sanquin, Amsterdam, The Netherlands).

Results

In un-stimulated cultures no detectable IFNγ was found, as was the case in un-infected controls exposed to *Coxiella antigens in vitro*.

Patients with active chronic Q fever (endocarditis, vascular infection), currently being treated with antibiotics showed high concentrations of IFNγ (FIG. 1). Patients recovered from uncomplicated acute Q fever did show an intermediate response (FIG. 1). In a second study a large cohort of individuals (n=1527) was screened before vaccination. These individuals lived in a region with high exposure risk to *Coxiella burnetii*. After screening the IFN-γ levels were correlated with positive skin test of serology for *Coxiella burnetii*. Individuals (n=346) that have been exposed to *Coxiella burnetii* before display a high production of IFN-γ (FIG. 2). This in contrast to individuals that had no positive skin or serology test (FIG. 2)

The invention claimed is:

1. A method for diagnosing Q-fever in a subject, wherein said subject has not been vaccinated with a vaccine against Q-fever, the method comprising the steps of:
   (a) contacting a sample obtained from said subject with a source of a *Coxiella burnetii* antigen, wherein said sample is whole blood or diluted whole blood;
   (b) determining the expression of a pro-inflammatory cytokine in said sample at the end of step (a); and
   (c), diagnosing Q-fever in said subject when a detectable expression level or an increase of the expression level of a pro-inflammatory cytokine is determined in step (b), wherein the pro-inflammatory cytokine is IFN-7.

2. The method according to claim 1, wherein the expression level of IFN-γ is determined by directly quantifying the amount of IFN-γ and/or indirectly by quantifying the amount of a nucleotide sequence encoding IFN-γ.

3. The method according to claim 1, wherein said source of a *Coxiella burnetii* antigen is a heat-inactivated or formalin fixated whole *Coxiella burnetii* cell.

4. The method according to claim 1, wherein acute Q-fever infection, chronic Q-fever or post Q-fever fatigue has been diagnosed.

5. The method according to claim 1, wherein Q-fever is diagnosed in said subject when an increase of at least 150% in the expression level of IFN-γ is determined in step (b) relative to a reference expression level of IFN-γ.

6. The method according to claim 5, wherein the reference expression level of IFN-γ is the expression level of IFN-γ in a control sample obtained from one or more healthy subjects.

7. The method according to claim 6, wherein the reference expression level of IFN-γ is the average value of the expression level of IFN-γ from multiple healthy subjects.

* * * * *